United States Patent [19]

Venema et al.

[11] Patent Number: 5,209,742
[45] Date of Patent: May 11, 1993

[54] CURVED CATHETER WITH ECCENTRIC LUMEN

[75] Inventors: Hendrik J. Venema, PD Roden; Arnoldus C. J. M. Wijkamp, AW Roden, both of Netherlands

[73] Assignee: Cordis Corporation, Miami Lakes, Fla.

[21] Appl. No.: 579,823

[22] Filed: Sep. 10, 1990

[30] Foreign Application Priority Data

Sep. 13, 1989 [NL] Netherlands ............ 8902286

[51] Int. Cl.$^5$ ............................................ A61M 25/00
[52] U.S. Cl. ......................................................... 604/281
[58] Field of Search ................................ 604/280–282, 604/95; 128/656, 658

[56] References Cited

U.S. PATENT DOCUMENTS

| | | | |
|---|---|---|---|
| 1,879,249 | 10/1932 | Honsaker | 604/280 |
| 4,033,331 | 7/1977 | Guss et al. | |
| 4,368,023 | 1/1983 | Hannah et al. | |
| 4,617,019 | 10/1986 | Fecht et al. | 604/280 |
| 4,735,620 | 4/1988 | Ruiz | |
| 4,820,262 | 4/1989 | Finney | 604/281 |
| 5,078,684 | 1/1992 | Yasuda | 604/281 |

FOREIGN PATENT DOCUMENTS 0063859 11/1982 European Pat. Off. .
8902281 3/1989 PCT Int'l Appl. .

Primary Examiner—John D. Yasko
Assistant Examiner—Anthony Gutowski
Attorney, Agent, or Firm—Gerstman & Ellis, Ltd.

[57] ABSTRACT

A catheter is made by extrusion of flexible plastic to form a tubular basic catheter body with a central channel. A curved end part is formed in one end thereof, with the central channel lying in eccentric relation inwardly toward the inside of the curved part to define a relatively thin catheter wall inwardly of the curve and a relatively thicker catheter wall outwardly of the curve of the curved part. Side holes may be punched into the curved part, with the side holes being of larger size without buckling of the side holes as the curved part of the catheter is straightened out. Such a catheter may be manufactured by a process including the step of inserting a metal wire which defines the required catheter curve into the central channel; heating the catheter end part with the metal wire therein to a temperature which is close to the catheter softening temperature, while permitting free rotation of the catheter about the wire, so that the wire causes the plastic memory of the catheter to deform to the desired curve; and subsequently cooling the catheter and removing the metal wire.

2 Claims, 2 Drawing Sheets

CURVED CATHETER WITH ECCENTRIC LUMEN

BACKGROUND OF THE INVENTION

The invention relates to a method for the manufacture of a catheter such as a nephrostomy drainage catheter or any other catheter, comprising (1) the extrusion from flexible plastic of a tubular basic catheter body with a central channel or lumen, (2) the attachment to one end of the basic body of a coupling element or hub, (3) the deformation of the opposite end part into a curved form, and (4) the providing in the curved end part of a number of side-openings connecting the central channel to the outside.

A drainage catheter, in particular a nephrostomy catheter, manufactured according to this per se known method is placed into an elastic, deformed and straightened state for insertion into the patient. The known drainage catheters of this type have the drawback that they can have only small discharge openings, because otherwise the wall in the vicinity of the side-openings may form sharp, outer ridges. When the side-openings are arranged in the end part, for example by punching while the latter is in the curved form, sharp ridges occur when straightening takes place. When the openings are punched in the straightened form of the catheter tip, the wall buckles sharply outward in the curved state of the catheter end.

Since a sharply buckled wall portion causes danger of injury either when it is being inserted into the patient or in the inserted position, it is necessary to avoid this buckling. Thus only small side-openings are used. The drainage capacity of the catheter is however limited as a result, and small drainage openings are moreover more easily obstructed by a blockage.

The invention now has for an object a method for the manufacture of a drainage catheter as described above, whereby larger side-openings can be employed without the danger of buckling of the wall in the vicinity of these side-openings.

DESCRIPTION OF THE INVENTION

With the method according to the invention this object is achieved in that the basic body is extruded such that the central channel or lumen thereof lies eccentrically in the basic body. Then, during the usual plastic deformation of the end part into a curve, by this invention the basic body is supported for free rotation about its lengthwise (longitudinal) axis, and the formation of the side-openings takes place after the end part has been plastically deformed into the curved state. The buckling of the wall portions does not occur with catheters manufactured in this manner, because, during straightening in use, the thin wall portion defined by the eccentric location of the central channel is normally stretched as it is straightened, while the thick wall portion does not crumple inwardly or buckle sharply outwardly because of its greater stiffness. The condition for achieving this is that the thin wall portion is situated on the inside of the end part bend, while the thick wall portion is situated on the outside thereof. In a surprising yet in retrospect explicable manner, it has been found that by supporting the basic body for free rotation about its lengthwise axis during the plastic deformation of the end part, the basic body automatically rotates such that the thick wall portion comes to lie on the outside of the bend and the thin wall portion on the inside of the bend.

The method according to the invention is simple to perform, and provides a drainage catheter which can be provided with larger side-openings without there being the slightest risk that the wall portions in the vicinity of the side-openings will form sharp, outward ridges. The method may be performed manually, if desired.

According to a preferred embodiment of the method according to the invention, the distal tip of the curved end part is formed into off-center, generally conical shape by grinding of the like, which conical shape is centered on the distal end of the central channel rather than the catheter axis. As a result, the central channel extends centrally into the pointed, distal end of the catheter.

The method according to the invention can be performed in a simple manner by inserting a metal wire with the required curved form into the central channel, heating said catheter end part with said metal wire therein to close to the catheter to softening temperature while said free rotation is provided, and subsequently cooling said catheter and removing said metal wire. Such use of a metal wire with the desired curve of the catheter provides in a simple manner that the basic body is supported for free rotation about its lengthwise axis during deformation, to achieve the results of this invention. The catheter may be made of a thermoplastic material such as nylon or P.E.T. to achieve this result.

The invention also relates to and provides a drainage catheter such as a nephrostomy catheter comprising a flexible, tubular basic body with a central channel which is fixed with one end in a coupling element or hub, and comprises at the opposite end the plastically deformed curved part described above, whereby in the curved part is provided a number, typically a plurality, of side-openings connecting the central channel to the outside. According to the invention, at least in the curved end part wherein the side-openings are arranged, the central channel lies shifted eccentrically toward the inner side of the bend, and at least some of the side openings are carried on a continuously curved portion of the curved part. Thus, when the catheter is straightened, the wall portions in the vicinity of the side openings do not buckle sharply outwardly.

DESCRIPTION OF THE DRAWINGS

The invention will be further elucidated in the following description with reference to the annexed figures.

DESCRIPTION OF THE SPECIFIC EMBODIMENTS

Figure 1:
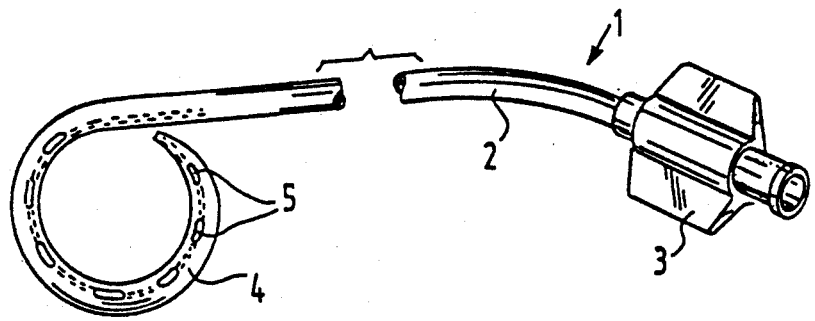
FIG. 1 shows in partial perspective view a catheter manufactured by the method according to the invention.

The catheter of FIG. 1 is a drainage catheter such as a nephrotomy catheter. This catheter 1 comprises a basic catheter body 2 of flexible plastic. The basic body 2 has a central channel or lumen 8. Attached to one end of the basic body 2 is a coupling element or hub 3.

The opposite end part or distal tip 4 is plastically deformed into a curved shape. In this plastically deformed, curved end part a number of side-openings 5 are formed. When the catheter is introduced into a patient the curved end part 4 is elastically straightened, and when the catheter has been placed in position, tensioning of the end part 4 is released, and it again assumes its curved form.

Figure 2:
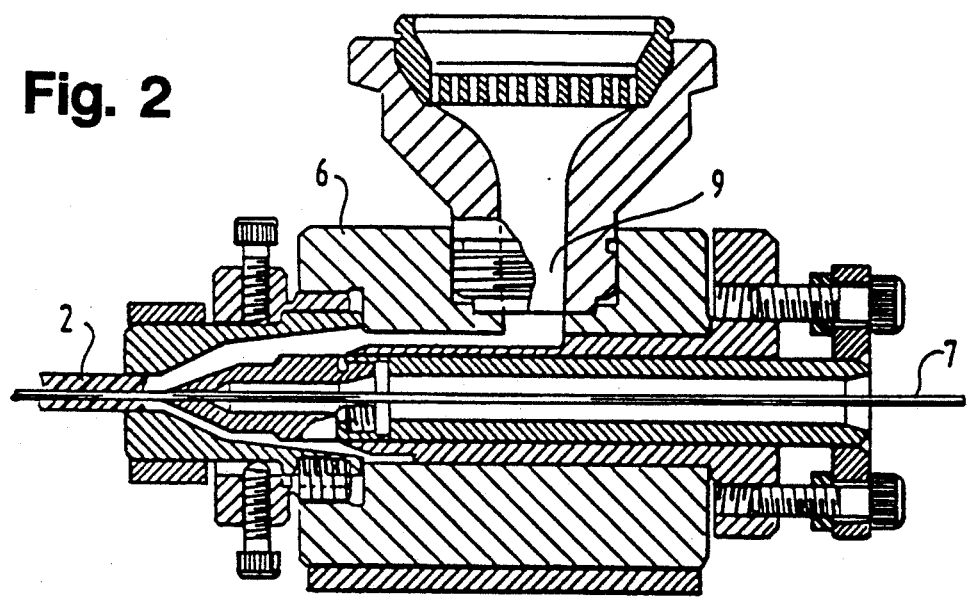
FIG. 2 shows a schematic section of an extrusion head as used with the method according to the invention.

As FIG. 2 shows the tubular basic body 2 is extruded in a per se known manner. FIG. 2 shows schematically an extrusion head 6 into which flexible plastic in plastic form is fed under pressure at inlet 9. Plastic leaves the extrusion head 6 on the left-hand side in tubular, coherent form, this being in the form of the flexible, tubular material for the basic body 2.

A core thread 7 around which the plastic is extruded is introduced eccentrically into the extrusion head. This core thread is later removed.

The material for the basic body 2 can thus be extruded in unlimited lengths, whereby for each catheter to be manufactured a piece of the material can be cut off at the appropriate length.

Figure 3:
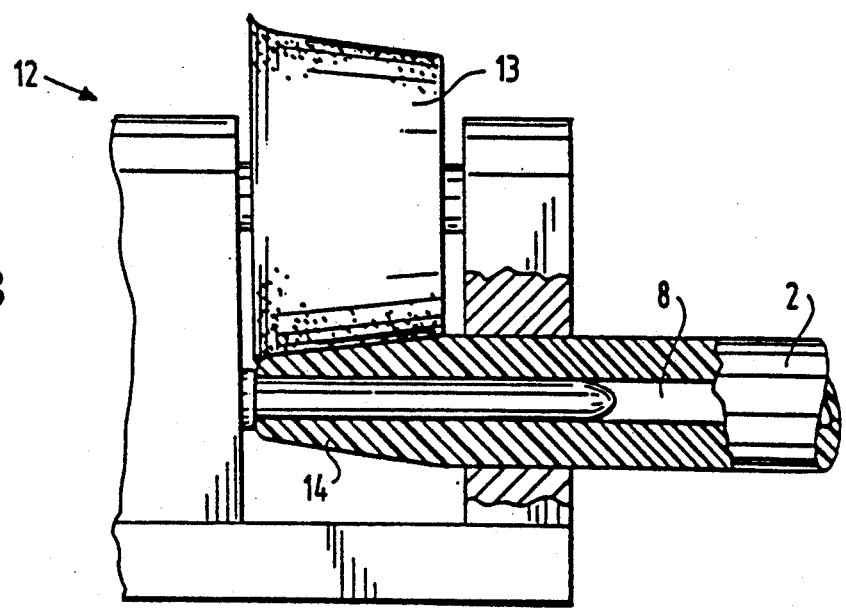
FIG. 3 is a partly broken away perspective view for the elucidation of the method step for forming a generally conical tip on the catheter.
Figure 4:
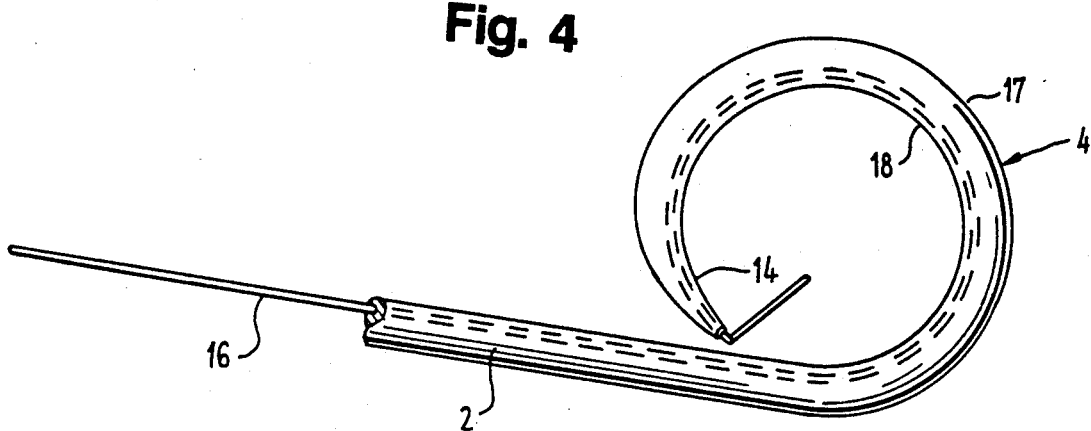
FIG. 4 is a perspective view showing the step of the plastic deformation of the end part of the catheter.

As FIG. 3 shows, after cutting off the basic body 2 from the starting material, one end thereof is given a generally conical point 14. This takes place using a grinding device 12 comprising a grindstone or grinding wheel 13. During grinding of the point 14, the basic body 2 is centered on central channel 8 rather than the catheter axis. This grinding step is carried out by providing the grinding device 12 with a pin onto which the basic body is pushed with the pin extending into the central channel 8. Centering of the basic body 2 on the central channel 8 during the point forming at the catheter distal end assures that the extension of the central channel 8 at its outermost point comes to lie concentrically to point 14, which point 14 assumes an asymmetric, irregularly conical shape.

After forming of the point 14, the end part 4 of the basic body 2 is plastically deformed into the curved form as shown. To this end, a metal wire 16 with the required curved form is pushed into the central channel 8. The end part 4 thus deforms elastically into the desired curved form. To make this form permanent, the end part 4 is heated with the metal wire 16 still therein, and then cooled, with the result that the desired curved form becomes fixed or set in the end part 4. The metal shaping wire 16 can now be removed, and the end part 4 normally takes the shape of its new curved form.

Because, during the plastic deformation of the end part 4, the basic body is supported for free rotation about its lengthwise axis by the metal thread 16, the end part automatically assumes the position which corresponds with the state of minimum energy. This means that the thickest portion of the diameter of the end part 4 comes to lie on the greatest possible radius, and therefore the thick wall portion 17 (FIG. 6) comes to lie on the outer side of the bend, while the thin wall portion 18 comes to lie on the inside of the bend.

Figure 5:
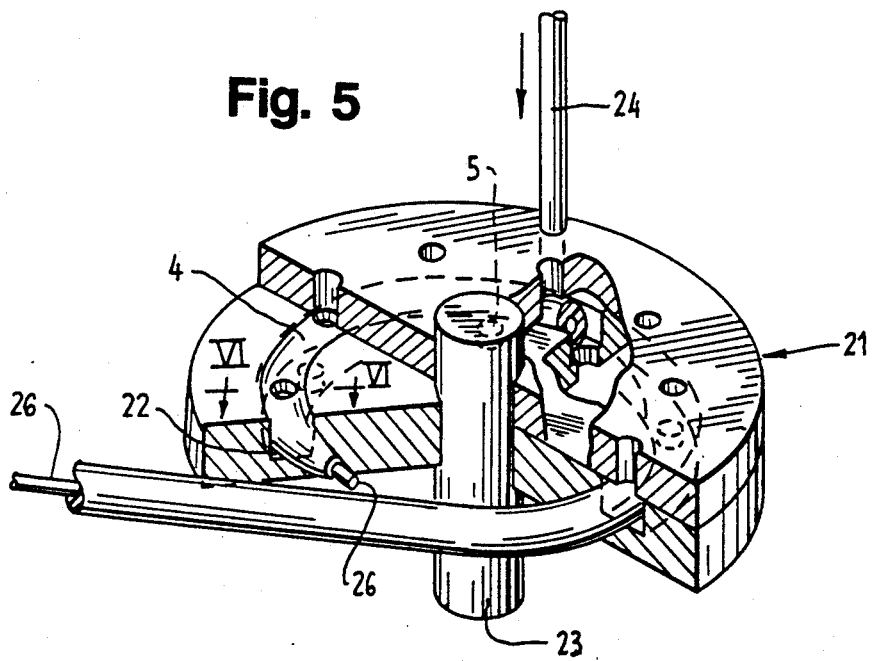
FIG. 5 is a partly broken away perspective view, showing the method step of forming the side-openings.

After the end part 4 has been given a curved form in this way, the side-openings 5 can be punched therein. As FIG. 5 shows, for this purpose of hole punching, the end part 4 is laid in a mold 21 in which is arranged a fixing groove 22 corresponding with the curved shape of the end part 4.

A punch 24 is attached to an up and downward movable holder and lies eccentrically relative to the mold 21, which is rotatable around the shaft 23. Inserted into the central channel of the catheter is a nylon thread 26 which serves as stop for the punch 24. One hole 5 is typically punched at a time, the mold then being turned to the following position and the next hole being punched. When one side is finished, the mold, with the catheter, may be turned over and the other side may be punched. After punching the nylon thread 26 is removed.

Figure 6:
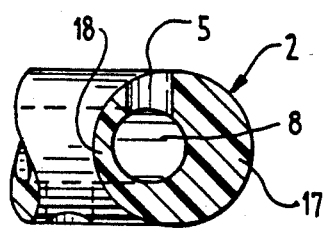
FIG. 6 shows a cross-sectional view of the catheter along the line VI—VI in FIG. 5.

As FIG. 6 shows, the punch blade 24 is positioned such that it lies directly above the central channel 8 in the end part 4.

Because the thick wall portion 17 lies on the outer side in the curved end part, when this end part is straightened, the thin wall portion 18 which is located on the inner side of the bend is subject to tensile loading or stretching, while the thick wall portion 17 which is located on the outer side of the bend is subject to pressure loading or compression. The thin wall portion does not, of course, buckle sharply outwardly when straightened because of the tensile loading. The thick wall portion does not, however, buckle either, because of the greater stiffness resulting from the greater wall thickness. The side-openings 5 can thus be larger than in prior art embodiments.

The above have been offered for illustrative purposes only, and is not intended to limit the scope of the invention of this application, which is as defined in the claims below.

That which is claimed is:

1. A catheter comprising a flexible, tubular basic catheter body defining a single lumen which carries at one end a coupling hub and which defines at the opposed end a curved tip in its natural, unstressed condition; and side-opening means defined in said curved tip connecting the lumen to the exterior, the improvement comprising, in combination:

the lumen in said curved tip being positioned eccentrically toward the inside of the curve of said curved tip, whereby the sidewall portion of said catheter body on the inside of the curve of said curved tip is thinner than the sidewall portion of said catheter body on the outside of the curve of said curved tip, and, upon straightening of said catheter tip in use, the thinner sidewall portion on the inside of said curved tip is placed into tension, while the thicker sidewall portion is placed into compression, with the result that buckling of the catheter wall adjacent said side opening means upon such straightening is suppressed, said side-opening means comprising side holes positioned on said curved tip in a lateral area between the thinnest and the thickest wall portions of said catheter tip.

2. The catheter of claim 1 in which the end thereof defined adjacent said curved tip is generally conically tapered toward a point positioned on the axis of said eccentric lumen.

* * * * *